United States Patent [19]

Brånemark

[11] Patent Number: 5,769,852
[45] Date of Patent: Jun. 23, 1998

[54] IMPLANTABLE ANCHORING ELEMENT AND ANCHORING ASSEMBLY FOR PROSTHESES

[75] Inventor: Per-Ingvar Brånemark, Molndal, Sweden

[73] Assignee: Medevelop AB, Sweden

[21] Appl. No.: 644,698

[22] Filed: May 10, 1996

Related U.S. Application Data

[63] Continuation of Ser. No. 233,526, Apr. 26, 1994, abandoned.

[30] Foreign Application Priority Data

Apr. 27, 1993 [SE] Sweden .................. 9301405

[51] Int. Cl.6 ............ A61B 17/56; A61B 17/58
[52] U.S. Cl. .............. 606/65; 606/62; 606/72; 623/18
[58] Field of Search .......... 623/18, 21; 606/62, 606/65, 66, 72, 73

[56] References Cited

U.S. PATENT DOCUMENTS

| 4,870,957 | 10/1989 | Goble et al. ................. 606/73 |
| 5,041,139 | 8/1991 | Branemark ................... 623/21 |
| 5,098,435 | 3/1992 | Stednitz et al. . |
| 5,171,284 | 12/1992 | Branemark ................... 623/21 |
| 5,360,450 | 11/1994 | Giannini ...................... 623/21 |
| 5,443,482 | 8/1995 | Stone ........................ 606/73 |
| 5,540,688 | 7/1996 | Navas ........................ 623/17 |

FOREIGN PATENT DOCUMENTS

| 2628443 | 6/1976 | Germany . |
| 8812806 | 10/1988 | Germany . |
| 8909579 | 10/1989 | WIPO . |
| 9118556 | 12/1991 | WIPO . |

Primary Examiner—Paul B. Prebilic
Attorney, Agent, or Firm—Ostrolenk, Faber, Gerb & Soffen, LLP

[57] ABSTRACT

An anchoring screw (1) is disclosed for implantation in bone, consisting of a tissue compatible material for supporting prostheses, artificial joint components, or the like. The anchoring screw (1) has at least one slot (5, 5a) extending from its threaded outer surface at a distance from the insertion end (3). The slot (5, 5a) is arranged to receive a blanking element (6, 6a) which shields the slot (5, 5a) during the application of the anchoring screw (1) and its integration in a recess prepared beforehand in the bone during a healing stage. The blanking element (6, 6a) is replaced, after integration of the anchoring screw (1) with the bone, by a holder for a prosthesis, the holder including a web portion insertable into said slot. There is also disclosed an anchoring arrangement comprising at least one such anchoring screw and such a holder or coupling, and a method for application of such an anchoring arrangement in osseous tissue.

8 Claims, 9 Drawing Sheets

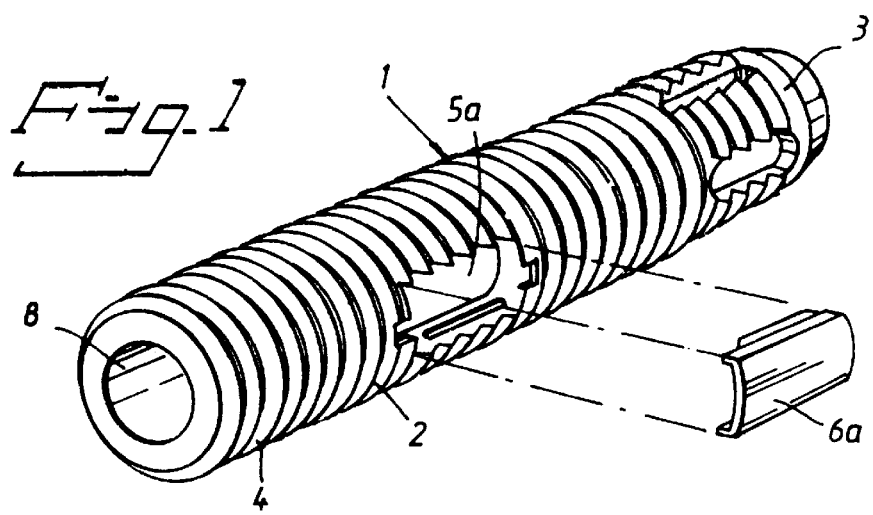
Fig. 1
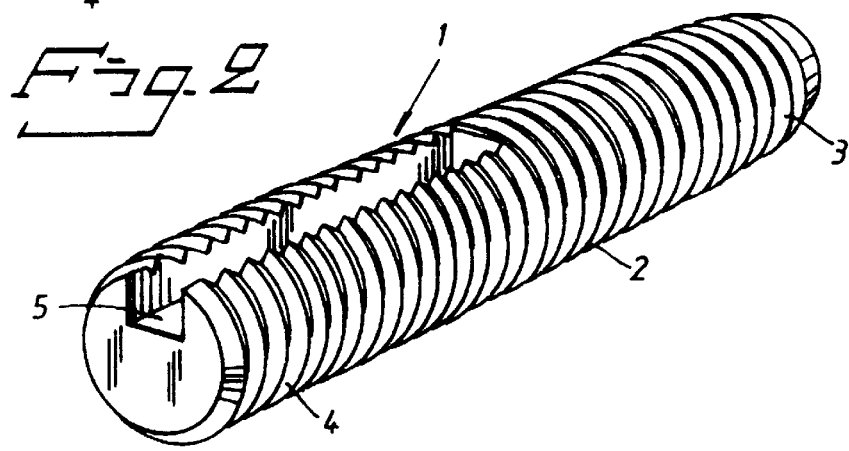
Fig. 2
Fig. 3  Fig. 4  Fig. 5  Fig. 6
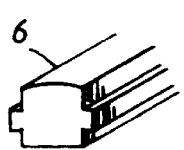 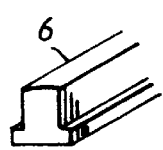 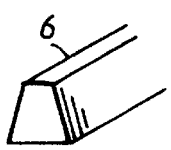 
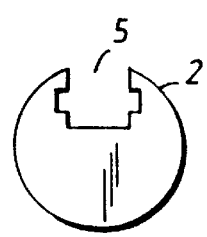 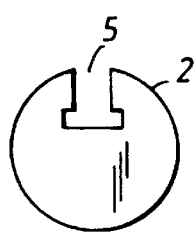 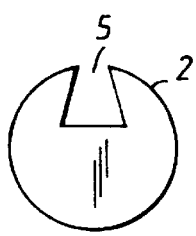 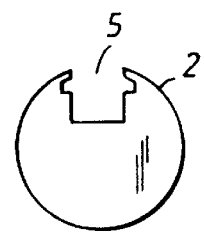

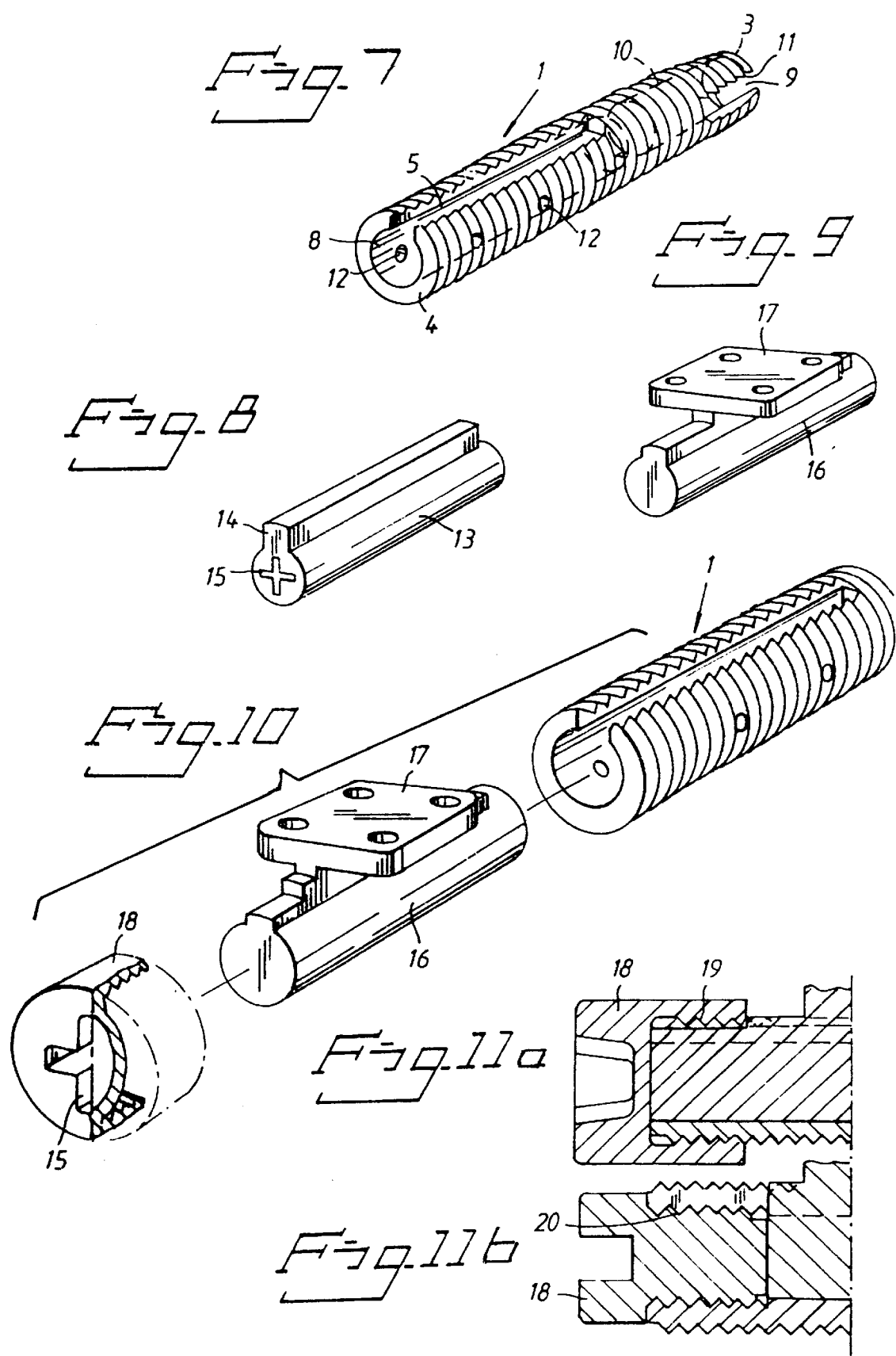

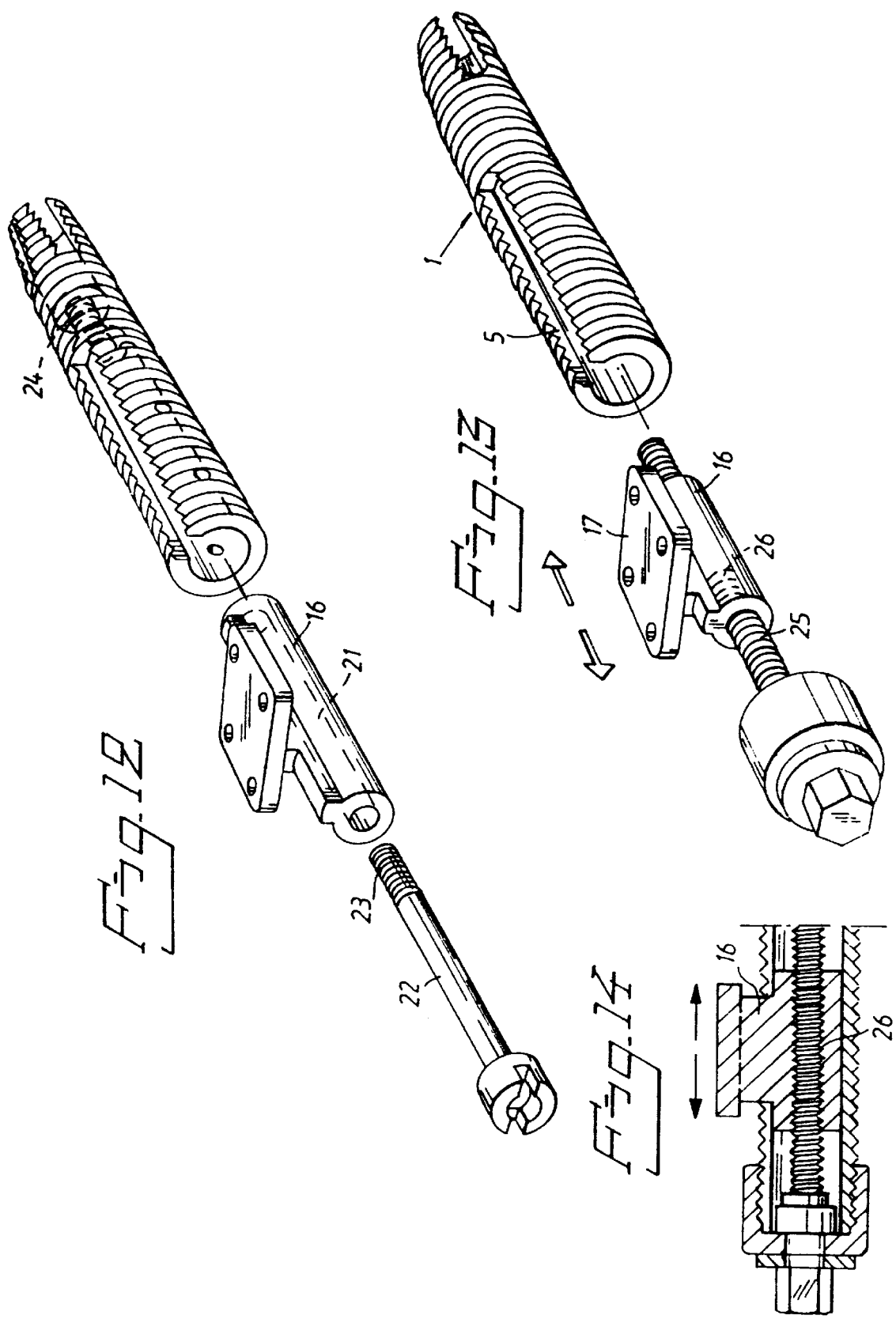

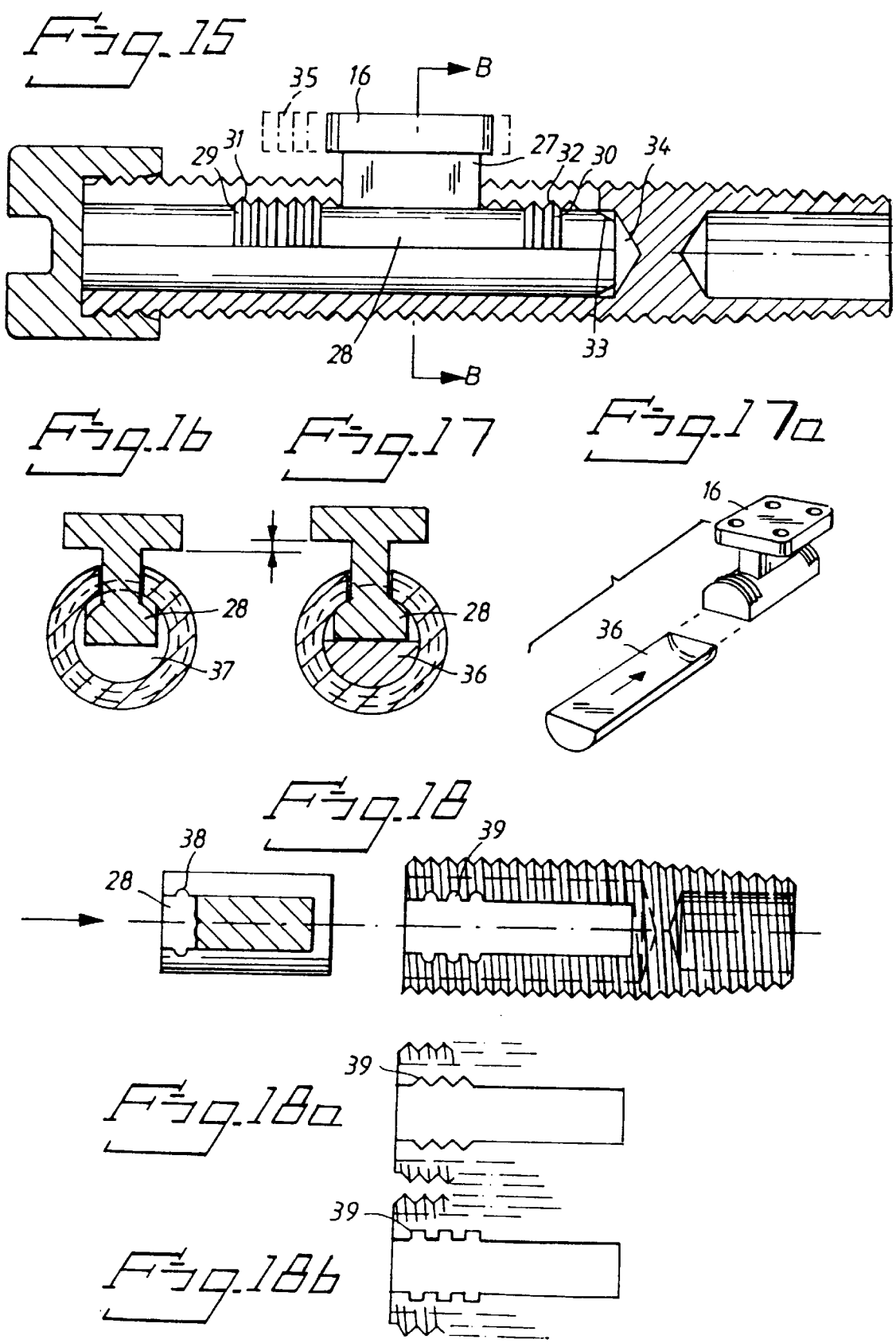

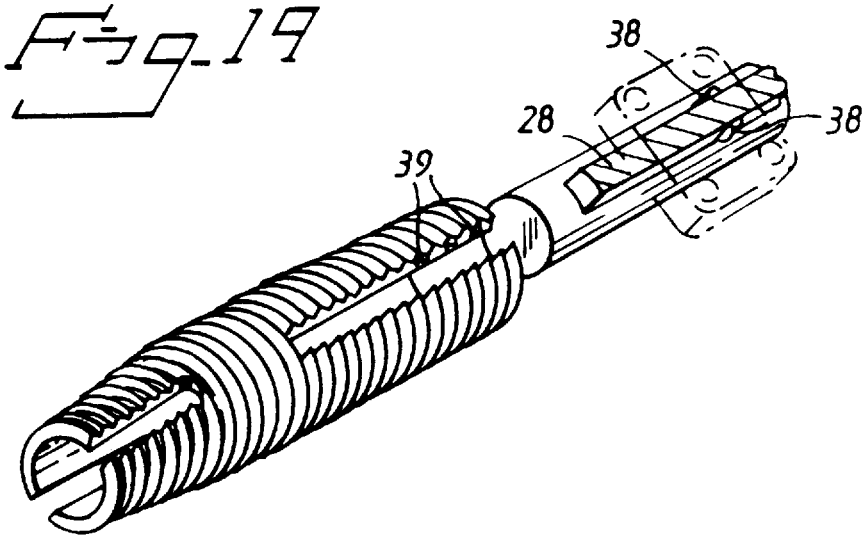
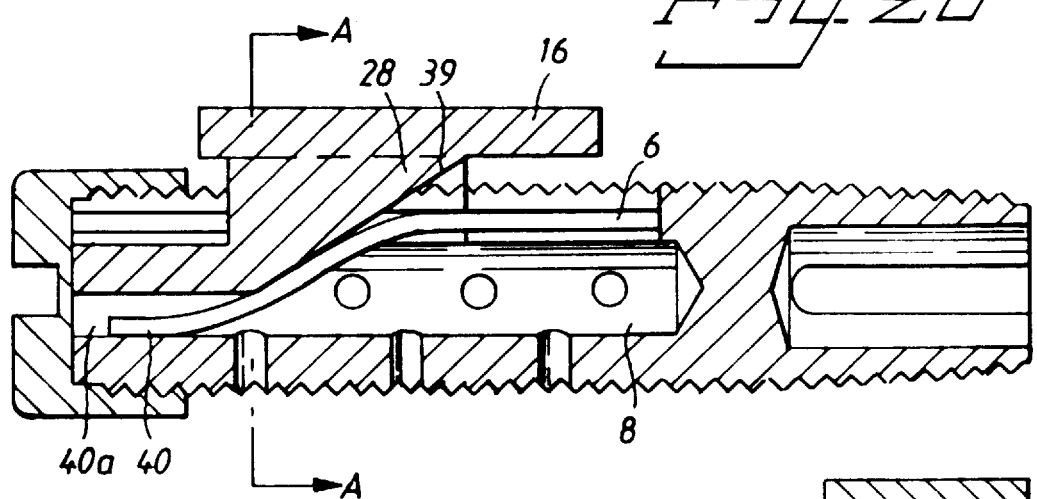
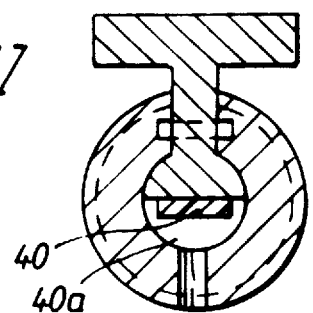

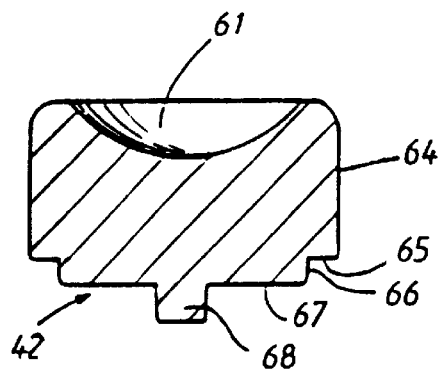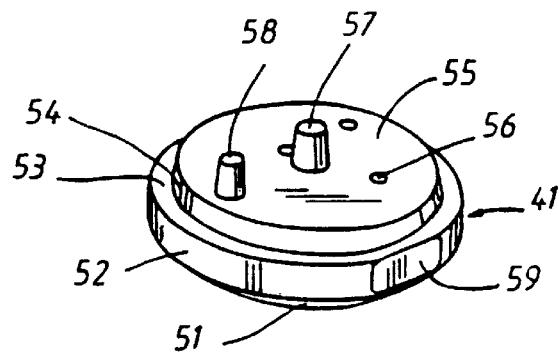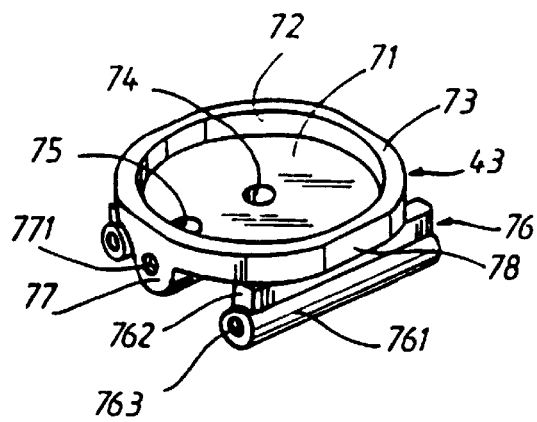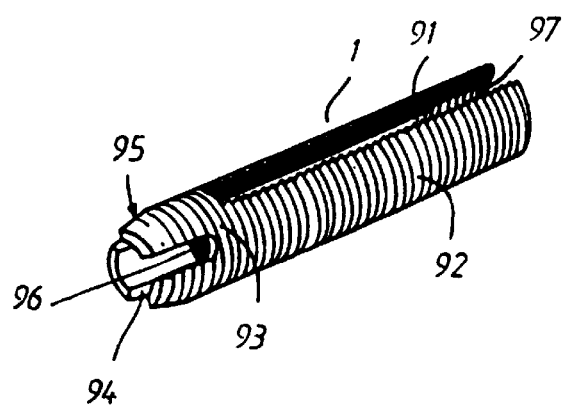

IMPLANTABLE ANCHORING ELEMENT AND ANCHORING ASSEMBLY FOR PROSTHESES

This is a continuation of application Ser. No. 08/233,526 filed on Apr. 26, 1994 and now abandoned.

BACKGROUND OF THE INVENTION

The present invention relates to a substantially rotationally symmetrical anchoring element intended for implantation in tissue, for supporting prostheses or the like, to apparatus including such an anchoring element, to an anchoring assembly comprising such anchoring elements and to a method of fixing such anchoring elements in tissue.

In a first aspect the invention relates to a rotationally symmetrical anchoring element for holding prostheses, artificial joint components or the like, said anchoring element consisting of a tissue compatible material, the anchoring element being provided with an external screw thread extending from an insertion end thereof towards an opposite, application end.

Such anchoring elements in the form of screws are known and described in, for instance, U.S. Pat. No. 5,064,425. Such anchoring elements have also been marketed by NobelPharma AB for a long time with great success, mainly within the dental field, under the trademark Branemark System®. As a rule, such anchoring elements consist of titanium and are provided with a micropitted and/or macropitted surface for achieving optimal osseointegration with surrounding bone tissue. Examples for such surface treatments are described in, for instance, U.S. Pat. No. 4,330,891.

Very often, and particularly in dental applications, these screws experience mainly axial loads applied by artificial teeth or dental bridges supported by the anchoring elements via suitable spacer elements.

More recently such anchoring elements in the form of screws have also been used for anchoring fixtures for, for example, artificial hip joint, ankle joint and hand joint constructions. U.S. Pat. No. 5,041,139 and U.S. Pat. No. 5,108,444 disclose arrangements in which such anchoring screws are anchored in bones perpendicular to the longitudinal direction of the bone.

SUMMARY OF THE INVENTION

One object of the present invention is to provide an anchoring element of the general kind referred to above, the anchoring element being, however, adapted to carry both axial and radial loads exerted by prosthesis and artificial joint components, etc., designed for direct attachment to the anchoring element or for attachment to the anchoring element via appropriate spacer elements.

Another object of the invention is to provide an anchoring arrangement including one or more such anchoring elements and an implant body connectable with the anchoring element or elements, the anchoring arrangement being adapted for optimal positional fixation in a space dissected out in bone tissue beforehand, and which also provides the possibility for direct coupling with a prosthesis element (or a further prosthesis element since the implant body may itself be regarded as a prosthesis element). Such an anchoring arrangement, in a preferred embodiment, affords substantial advantages in terms of surgical technique and in particular allows a substantial reduction in the number of coupling parts needed for various kinds of coupling arrangements. The space needed by the preferred form of anchoring arrangement embodying the invention is also substantially less than for known anchoring arrangements.

According to one aspect of the invention, there is provided a substantially rotationally symmetrical anchoring element intended for implantation in tissue for supporting prostheses, artificial joint components or the like, the anchoring element consisting of a tissue compatible material, said anchoring element being provided with an external thread, the anchoring element having an insertion end and an application end, the anchoring element having a slot extending into the element from the peripheral surface of the element at a distance from the insertion end.

According to a preferred embodiment of the invention said slot is arranged for releasably receiving a blanking element shielding the slot during the application and healing stages. After the element has been firmly anchored in the tissue it is possible, for instance, to replace the blanking element by a prosthesis holder to be inserted into the slot after removal of the blanking element.

Said slot may be a track milled in the anchoring element, the lateral edge surfaces of the slot being arranged for releasable retention of said blanking element.

In a preferred embodiment of the invention an inner bore extends from the application end of the anchoring element and the slot communicates with the bore and also extends from the application end. The length of the bore is equal to or greater than that of the slot.

Preferably the blanking element has a root portion shaped and dimensioned to allow it to be inserted in said bore and has an extension portion of reduced thickness extending from said root portion such that the blanking element can be releasably fitted in the anchoring element from said application end with the root portion within said bore and said extension portion of reduced thickness extending through and substantially filling said slot.

The blanking element can be removed from the axial bore after osseointegration of the anchoring element with surrounding tissue and can be replaced by a prosthesis component having a portion corresponding in form to that of the blanking element and which, when inserted into the slot, thus occupies the slot and part of the axial bore. The prosthesis component for thus inserting in the anchoring element may take the form of a holder for a further prosthesis component such as an artificial joint part.

According to a further embodiment the slot can be formed with lateral grooves extending substantially perpendicular to the axis of the anchoring screw for cooperation with complementary lateral ribs on the prosthesis component for location of the prosthesis component longitudinally with respect to the anchoring screw.

After insertion of the anchoring element into the tissue the blanking element can be readily replaced by a prosthesis component in the form of a holder having a part of the same form and design as the blanking element for engagement with the anchoring screw, the holder including a base plate for securing further prosthesis components.

The invention also relates to anchoring assemblies provided with one or more anchoring elements in accordance with the invention. Such anchoring assemblies may be used, for example, for reconstruction of joints, such as ankle joints, knee joints, hip joints, arm joints, etc.

One such anchoring assembly for a joint prosthesis intended for anchoring in osseous tissue comprises at least one substantially rotationally symmetrical anchoring element intended for implantation in tissue and consisting of a tissue compatible material, for holding prostheses, artificial joint components or the like, the anchoring element being provided with external threads extending from its application end towards its insertion end, the anchoring element having, at a distance from the insertion end, at least one slot arranged in the threaded peripheral surface of the anchoring element, the anchoring element being adapted for screwing into a bore prepared beforehand and adjacent to a joint and substantially parallel with the joint axis or the joint plane, the anchoring element being, via the slot, arranged for releasably holding a prosthesis component intended for use as an artificial joint body.

Such an anchoring assembly can comprise two or more anchoring elements and may include an implant body provided with two or more coupling means.

The invention, in another aspect thereof, provides a method of fixing an anchoring assembly for a joint prosthesis in the osseous tissue of a bone forming one of the elements in a joint, said method comprising dissecting out a space in the osseous tissue adjacent to the joint selected for replacement, the space being provided with a cross sectional profile substantially coinciding with the cross sectional profile of the anchoring assembly, the anchoring assembly comprising at least one anchoring screw and an implant body releasably mountable on the anchoring screw, said space comprising at least one bore for receiving the anchoring screw and extending parallel with the joint axis or the joint plane, and one space for receiving the implant body and communicating with the bore, the method including screwing the anchoring screw into the bore, inserting the implant body into the space communicating with the bore and releasably coupling the implant body to the anchoring screw, allowing the anchoring screw and the implant body to integrate with osseous tissue during the healing process, uncovering the side of the implant body facing the joint and releasably securing a joint element to the uncovered side of the implant body.

Embodiments of the invention are described below by way of example with reference to the accompanying drawings.

BRIEF DESCRIPTION OF THE DRAWINGS

FIG. 1 is a perspective view showing a first embodiment of the invention,

FIG. 2 is a perspective view of a second embodiment,

FIGS. 3 to 6 show perspective views of various forms of blanking elements and sectional views of complementary anchoring elements, FIG. 7 is a perspective view of a third form of anchoring element embodying the invention, FIG. 8 is a perspective view showing a blanking element, and a corresponding prosthesis component, FIG. 9 is a perspective view of a prosthesis holder, FIG. 10 is a perspective exploded view showing part of the anchoring element of FIG. 7 with the associated prosthesis component of FIG. 8 and also showing a stop screw which also is partially shown in section, FIGS. 11a and 11b show, in axial section view the application ends of two different forms of anchoring element embodying the invention, with respective different kinds of stop screw, FIG. 12 shows, in exploded perspective view another combination of anchoring element, prosthesis component and stop screw all embodying the invention, FIG. 13 is an exploded perspective view similar to FIG. 12 but showing a variant, FIG. 14 is a partial, axial section view of the variant of FIG. 13 in an assembled state, FIG. 15 is a longitudinal section view of a further embodiment of the invention, with a prosthesis component in the form of a holder for a further prosthesis part inserted in an anchoring screw, FIGS. 16, 17 and 17a are cross-sectional views, along the line B—B of FIG. 15, respectively with a retaining wedge removed and with the retaining wedge fitted. FIG. 17a also shows, to the right, an exploded perspective view of the holder and the retaining wedge, FIG. 18 shows in the upper position, partly in plan and partly in section a portion of a prosthesis component insertable in an anchoring screw and the complementary anchoring element, and FIGS. 18a and 18b show fragmentary plan views of two alternative anchoring screws, FIG. 19 is a perspective view of an anchoring screw and part of a prosthesis component, of substantially the form shown in the upper position in FIG. 18, FIG. 20 is a view in longitudinal section through a further anchoring screw, blanking element and prosthesis holder embodying the invention, FIG. 21 is a view in cross-section along line A—A in FIG. 20, FIG. 26 is a view in vertical section through the tibia socket of FIG. 24, perpendicular to the axes of the anchoring screws, FIG. 27 shows, in perspective, one side of a component which provides, on its opposite side, the talus ball of the joint of FIG. 22, FIG. 28 shows, in perspective, a component which holds the component of FIG. 27, the perspective view being from the side to which is fitted the side of the component of FIG. 27, which is visible in FIG. 27, the component of FIG. 28 being herein referred to as the talus implant holder, FIG. 29 shows an anchoring screw of the joint of FIG. 22, in perspective view and with the slot shown.

DESCRIPTION OF PREFERRED EMBODIMENTS

Figure 22:
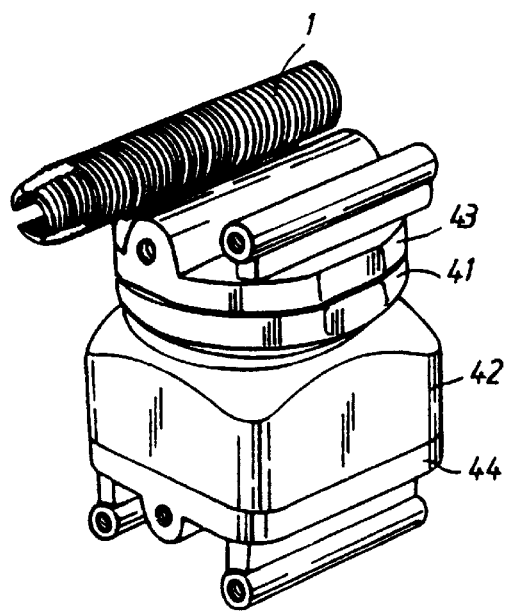
FIG. 22 is a perspective view of an artificial ankle joint with two anchoring assemblies embodying the invention for anchoring in the talus and the tibia, respectively, only one of four anchoring elements being shown, the joint being shown in inverted position for purposes of illustration.

FIG. 1 of the drawings shows a first form of anchoring element 1 embodying the invention.

The anchoring element 1 has the general form of a screw with an external screw thread 2 which, in the embodiment shown, extends from one end of the screw to the other. One end 3 of the screw is somewhat conically tapered and, in the following, will be designated the "insertion end", because it is the end which is the first inserted into the bore prepared in the bone tissue in use of the anchoring element, prior to screwing the element into such bore. In the following the opposite end 4 of the screw will be designated the "application end".

The anchoring element shown in FIG. 1 is provided with a longitudinal axial bore 8 extending from the application end 4. The element 4 is also provided with a slot or recess 5a in its peripheral surface. Recess 5a is initially covered by a blanking element 6a releasably secured within the recess 5a. Blanking element 6a thus closes slot or recess 5a when element 1 is being screwed into a bore prepared in tissue beforehand, and can, as will be described below, be easily removed to prepare the anchoring element for coupling with a prosthesis component which may, for example, be in the form of a holder adapted to receive other prosthesis components. The slot 5a is shown as being elongate in a direction parallel with the axis of element 1 but can, of course, alternatively be arranged to be elongate perpendicularly to the longitudinal axis of the anchoring element 1. By such a recess 5a, which is appropriately located half way along the element 1, it is possible, for the first time, to accomplish also transverse loading of the anchoring element. The slot 5a preferably extends as far as bore 8 and opens into bore 8. In the arrangement of FIG. 1 the slot 5a is relatively short and is closed at both ends. The longitudinal side walls of the slot 5a are formed with longitudinal grooves to receive laterally projecting ribs or tongues on the sides of the blanking element 6a which is preferably resilient enough to allow the element 6a to be snapped into place in slot 5a and to be levered out of slot 5a when desired.

The embodiment shown in FIG. 2 has, instead of a short slot 5a closed at both ends a slot 5 extending longitudinally from the application end 4 of the screw 1, towards the insertion end 3. As with the anchoring element of FIG. 1, during screwing-in of the anchoring element and during the subsequent healing process resulting in attachment of the screw to tissue, the slot 5 is occupied by a releasable blanking element. The side walls of the slot 5 can be grooved or otherwise formed in any of various ways for retention of blanking elements of complementary form. Thus, each of FIGS. 3 to 6 shows, at the top an end part of a blanking element 6 of a particular cross-sectional shape and, at the bottom, an end view (to a smaller scale) of an anchoring screw having a slot 5 of complementary cross-sectional shape. Preferably, the upper surface 7 of each blanking element 6 is somewhat rounded off and, thereby, forms a natural transition between the outer surface of the blanking element and the adjacent peripheral surface of the anchoring screw. The various forms of blanking element shown in FIGS. 3 to 6 in combination with the respective complementary cross-sections of slots 5, provide for good positional fixation of the blanking elements in the slots. The blanking element 6 can, of course, also be given other forms such as, for example, forms with straight lateral borders and a straight bottom section for insertion in the milled slot 5 shown in FIG. 2. The blanking elements 6 of FIGS. 3 to 6 can be inserted into and removed from their respective slots by longitudinal sliding. The blanking element 6 should, however, occupy the entire slot, and, for example, should be of the same length as slot 5, thereby efficiently preventing tissue from growing into the slot during the healing period of the anchoring element.

Suitably the anchoring screw 1 is of titanium or has at least an outer layer of titanium. For achieving optimal osseointegration with tissue, the anchoring element 1 may be provided over its outer surface with micropits and/or macropits, that is, pits located relatively close to each other and having a diameter of between 10 to 10,000 nm (micropits) and/or pits with a diameter of from 1 m$\mu$ up to 20 m$\mu$ and more (macropits). The micropits may be superimposed on existing macropits. Various techniques for production of such pitting of titanium surfaces are known.

Blanking insert 6 should consist of a material which does not readily become anchored in tissue; for instance, it can be of a plastic material suited for this purpose or a highly polished metal strip e.g. of titanium.

The basic idea is that the slot 5, 5a, arranged in the anchoring element should be covered by a releasable blanking element 6, 6a, during insertion in a bore prepared in tissue beforehand, the blanking element serving to prevent tissue growth into the slot and the blanking element being easily removable at a later stage for replacement by a holder for prosthesis components, spacer means or other coupling means for prostheses or the like, said holder being insertable into the thus uncovered slot.

FIGS. 7 to 11 show a development of the basic principle illustrated in FIGS. 1 to 6.

As is evident from FIG. 7 the anchoring element 1 has an axial bore 8 extending from its application end 4 and communicating with a longitudinal slot 5. Preferably bore 8 extends somewhat longer towards the screw's insertion end 3 than slot 5 itself. The conically tapering insertion end 3 may also be provided with a second axial bore 10 extending from said insertion end and slots 9 may be formed in the screw, extending from end 3, the slots 9 providing cutting edges 11 to facilitate the screwing of the screw into the bore prepared in tissue beforehand. Bores 8 and 9 however do not communicate with each other. In addition inner bore 8 has a number of openings 12 for supply of, for instance, growth promoting or anti-inflammatory agents to the space between the tissue and the outer threads.

A blanking element 13 is shown in FIG. 8 which, in this embodiment is shaped and dimensioned for insertion into the bore 8. More particularly, the blanking element 13 has a generally cylindrical root portion of a size to fit snugly in the bore 8 and has an extension portion 14 of reduced thickness extending radially from the root portion and dimensioned to fit snugly in the slot 5. The radial dimension of the extension portion 14 is, of course, such that the radially outer surface thereof forms a natural extension of the peripheral surface of the anchoring screw. At its end which is at the insertion end of the screw 1 when the blanking element is fitted, the blanking element has in its end face a cross slot 15 for cooperation with a suitable screw-driving instrument (not shown) by which the anchoring element 1 with the blanking element in place, can easily be screwed into the bore prepared in tissue beforehand and can be readily adjusted to the desired angular position about its longitudinal axis. The extension portion 14 thus provides positively mechanically controlled transmission of rotational moments, applied to the blanking element 13, to screw 1.

FIG. 9 shows a prosthesis component, in the form of a holder 16 designed for fitting to the anchoring screw 1 after removal of the blanking element 13 after osseointegration of screw 1 with tissue. The holder 16 has a portion of substantially the same shape and size as the blanking element 13 and thus has a generally cylindrical root portion to fit snugly in bore 8, and an extension portion of reduced thickness such as to fit closely in the slot 5. However, the extension portion includes a portion which, when the holder is fitted, extends beyond the anchoring screw 1 and carries attachment means to which a further prosthesis part may be secured. In the arrangement shown in FIG. 9, this attachment means comprises a mounting plate 17 integral with the root portion and extension portion and provided with holes for mounting screws or bolts for securing a prosthesis component to plate 17.

FIG. 10 shows, in exploded perspective view, one portion of the anchoring element 1 illustrated in FIG. 7, with slot 5, bore 8, and the corresponding fitting holder 16 shown in FIG. 9 with root portion and extension portion respectively intended for insertion into bore 8 and slot 5. In addition there is shown in FIG. 10 a stop screw 18 adapted to be screwed onto the application end of screw 1 after the holder 16 has been fitted in order to close the application end 4 of screw 1 and hold the holder 16 captive while positionally securing holder 16 by preventing longitudinal movement of holder 16 relative to the anchoring screw 1. To this end, the length of the root portion of the holder 16 may correspond with the length of the bore 8 so that, as shown in the upper view in FIG. 11, the end of the root portion is flush with the application end of the screw 1 and is engaged by the inner end of the stop screw 18. The upper view in FIG. 11 is, a view in axial section, in a plane containing slot 5, of the end portion of the anchoring screw of FIGS. 2 and 10, with holder 16 and stop screw 18 fitted. Reference 19 in FIGS. 11*a* and 11*b* denote an internal screw thread in a skirt of screw 18 which takes the form of an internally threaded cap, the thread 19 being complementary to the external thread on screw 1. The lower view in FIGS. 11*a* and 11*b* show a variant in which the end of bore 8 adjacent the application end of screw 1 is internally threaded at 20 to receive an externally screw-threaded portion of a variant stop screw 18. As shown in FIGS. 10, 11*a* and 11*b*, the stop screw 18 is provided with a cross-slot 15 or other drive formation for engagement by a complementary driving tool for screwing up screw 18 onto or into the application end of screw 1.

Such locking of the holder 16 can also be accomplished by a simple stop screw which is positionally fixed by a prick punch.

In the variant illustrated in FIG. 12 the holder 16 has generally the same form as that of FIGS. 9 and 10 but additionally has an axial bore 21 extending through the cylindrical root portion for receiving a bolt 22. The bolt 22 has a threaded portion 23 extending to its front end, intended for cooperation with a corresponding internal thread 24 in a reduced diameter portion of bore 8 at the end of bore 8 furthest from application end 4.

The bolt 22 has a head which can fit within bore 8 at the application end of the screw 1, the head having a slot for a screwdriver. After insertion of the root portion of the holder in bore 8, the shank of bolt 22 can be passed through bore 21 and the threaded end 23 screwed into threaded bore portion 24 until the bolt head bears firmly against the end of the root portion nearer the application end, thereby locating the holder against axial movement relative to the anchoring screw.

The further variant shown in FIGS. 13 and 14 differs from that of FIG. 12 in that the shank of the bolt (referenced 25 in FIG. 13) is screw threaded over its whole length and the axial bore in the root portion of holder 16 is correspondingly internally screw threaded, with the bolt shank being thus in screw threaded engagement with the root portion. The end of the bolt does not, in this case, screw into a screw threaded bore in anchoring screw 1, but the head end of the bolt is retained rotatably, but axially immovably, in an end cap, having an internally screw-threaded skirt, which is screwed onto the external screw thread at the application end of the anchoring screw. The axial position of the holder 16 along the bolt 26 and thus along the anchoring screw, can thus be adjusted by rotation of the bolt 26, from its hexagonal head projecting from the end cap as shown in FIGS. 13 and 14, after fitting the holder 16 to the anchoring screw and after securing the end cap. Thereby it is possible to obtain an exact positional fixation of holder 16 along slot 5.

FIG. 14 shows partially, in axial section, the embodiment illustrated in FIG. 13 in an assembled state.

In a further variant shown in FIGS. 15, 16 and 17, the holder 16 has a root portion 28 which has a depth (as measured along a diameter parallel with the direction in which the extension portion (27) extends from the root portion) which is substantially less than the diameter of bore 8, whereby the holder 16 can move, relative to the anchoring screw 1, to a limited extent in the direction of radial extension of the extension portion from the root portion, and in the opposite direction. Furthermore, the surface of the root portion which is on the same side as said extension portion is provided with ribs 29, 30, which can cooperate with complementary grooves 31, 32 in the bore 8, on the same side of the bore 8 as the slot 5. A removable insert or wedge 36 can be inserted between the side of the root portion remote from the extension portion and the surface of bore 8 remote from the slot 5 to prevent the root portion from being moved away from the grooves 31, 32. With the insert or wedge 36 removed, a space 37 is formed below the root portion 28, as shown in FIG. 16, into which the root portion 28 can be displaced, whereby the axial position of holder 16 can be adjusted by pushing the extension portion (referenced 27 in FIG. 15) further into bore 8 to displace the root portion, with its ribs 29, 30, out of engagement with grooves 31, 32, adjusting the holder longitudinally in the anchoring screw 1, displacing the extension portion 27 radially outwardly again to bring the ribs 29, 30 into engagement with the grooves 31, 32 in the new position of the holder 16. The holder can be secured in its adjusted position by inserting the insert or wedge 36 into the space 37 between the root portion and the part of bore 8 opposite slot 5 to prevent displacement of the root portion such as to disengage the ribs 29, 30 from the grooves 30, 31. A stop screw screwed onto or into the end of the anchoring screw then holds the wedge or insert 36 in place and thus fixes the position of holder 16 relative to the anchoring screw. In the embodiment shown in FIGS. 16, 17 and 17*a*, the wedge or insert 36 is substantially semi-circular in cross-section, while the root portion 28 has a form which would be produced by relieving or chamfering lateral edge regions of a body of semi-circular cross-section to provide clearance for inward displacement of the root portion. The root portion 28 thus has a flat face which faces in the opposite direction from that in which portion 27 extends and which flat face cooperates with the flat face of wedge or insert 36. The ribs 29, 30 and grooves 34, 32, may be formed by respective segments of cooperating screw threads on the curved surface of root portion 28 and the opposing portion of bore 8 respectively. The frontal end portion 33 of holder part 28 directed towards the insertion end 3 is somewhat inclined and arranged to be received in a correspondingly inclined part 34 in the bottom of inner bore 8. In this way holder 16 can be easily adjusted into a selected one of the various positions indicated by dash dotted lines 35 in FIG. 15.

A further method (not shown in the drawings), of allowing for adjustment of holder 15 longitudinally in slot 5 is to make the root portion shorter than bore 8 and to provide a selection of different sizes of shims or packing pieces which can be inserted into inner bore 8 in front of and/or behind the root portion of the holder 16. A cap similar to one of the caps 18 of FIGS. 11a and 11b for example, could, in this case, be used to retain the root portion and packing pieces in the bore 8. In another variant, shown in FIG. 18 and in FIG. 19, the lateral faces of the extension portion 27, in the regions thereof which lie within the slot 5 in the fully installed position, are provided with respective ribs or protrusions 38 which can engage in selected ones of a plurality of grooves 39 formed in the lateral faces of the slot 5 at intervals therealong. It will be appreciated that the ribs 38 and grooves 39 extend generally radially with respect to the axis of the anchoring element. The radial extent of the ribs 38 is not significantly greater than the depth of the slot 5 and the root portion 28 has again substantially the general cross-sectional form, and dimensions relative to the bore 8, as in the embodiment of FIGS. 15 to 17, so that again the axial position of holder 16 along the anchoring screw can be adjusted by pushing the extension portion 27 radially inwards until the ribs 38 are disengaged from the ribbed side faces of slot 5, adjusting the holder 16 longitudinally of the slot and moving the holder radially outwardly of the anchoring screw to engage the ribs 38 in their new grooves. Once again, the holder 16 is fixed in its adjusted position by inserting wedge 36 into the space 37 below the root portion and screwing on the stop screw or end cap. The two lower views in FIG. 18 (FIGS. 18a and 18b) illustrate different possible cross-sectional shapes for the grooves 39. It will be appreciated that in each case the ribs 38 will be of complementary shape. It will also be appreciated that the ribs 38 could be provided on the lateral faces of the slot 5 and the series of grooves 39 formed in the lateral surfaces of extension 27, as an alternative to the arrangement shown.

In the embodiment shown in FIGS. 20 and 21 the slot 5 has lateral surfaces each provided with a longitudinal groove, and the blanking element 6 takes the form of a thin flexible strip which is inserted in slot 5 so that the lateral edges of the strip are engaged in these longitudinal grooves. As in the previous embodiments, the blanking element remains in place during implantation of the anchoring element and the subsequent healing. When the time comes to fit the holder 16 (shown already installed in FIGS. 20 and 21) it is not necessary to remove the blanking strip 6 in a distinct method step. Instead the front end of the root portion of holder 16 and of the extension portion 28 are shaped to provide an inclined ramp surface 39 which, as the root portion and extension portion are inserted respectively into the bore 8 and slot 5, engage the upper side of strip 6 and automatically force the strip 6 radially inwards into the inner bore 8. The root portion of the holder 16 is in the form of a cylinder cut away on its side remote from the extension portion which fits in the slot, so that once again a space is formed within bore 8 below the root portion, i.e. on the side of the root portion opposite the slot 5. This space, referenced 40a in FIGS. 20 and 21, receives the strip 6 after it has been forced downwards by the ramp face 39. In this embodiment the resilient strip 6, by bearing on the holder 16, serves to hold the latter in position. Furthermore, the unused portion of slot 5 remains covered by strip 6. The portion of strip 6 which has been forced downwards into space 40a is referenced 40 in FIGS. 20 and 21.

The design of the anchoring elements described with reference to the drawings provides, for the first time, conditions for arranging prosthesis components loading the anchoring element substantially perpendicular to its longitudinal direction, thereby providing for the first time optimal conditions for exploiting the transverse strength of the anchoring element. At the same time substantial advantages in respect of operation technique are thereby obtained, since a screw-formed anchoring element designed in this way also can be universally used for loads in the axial direction as well as loads perpendicular to the axial direction of the anchoring element. This results in the possibility of locating the anchoring element very close to a joint, in the dental field, for frontal application of the screw into the palate instead of, as is presently the case, from above.

Figure 23:
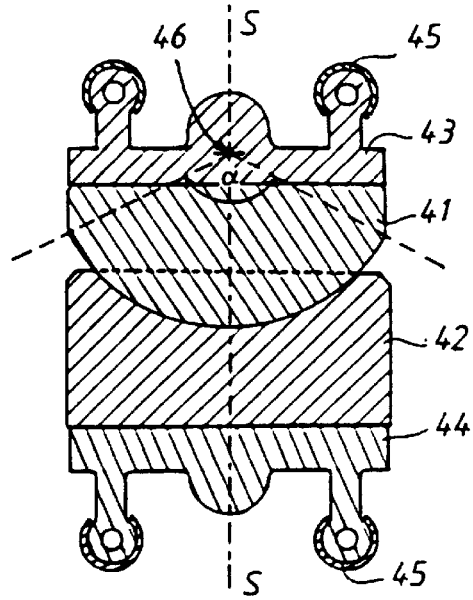
FIG. 23 is a view in vertical section through the center of the joint of FIG. 22 and perpendicular to the longitudinal axes of the attached anchoring screws, all four anchoring screws being shown.
Figure 24:
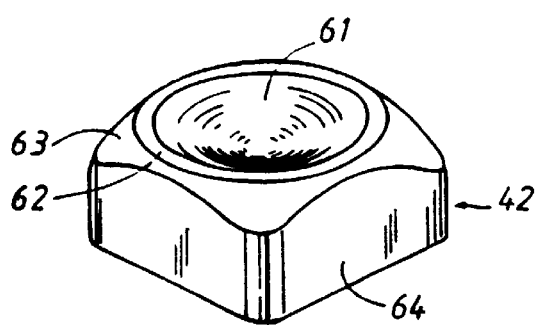
FIG. 24 is a perspective view which shows the tibia socket of the artificial joint of FIG. 22.

FIGS. 22 and 23 show, in perspective view and sectional view respectively, an artificial ankle joint consisting of a highly polished talus ball element 41 in alloyed titanium (Ti6A14V) and a tibia socket element 42 in high density polyethylene, in combination with a talus implant body 43 holding the talus ball element 41 and a tibia implant element 44 holding the tibia socket element 42. In FIGS. 22 and 23, for purposes of illustration, the artificial ankle joint is shown inverted with respect to its orientation when implanted in a patient. This inversion also applies to FIGS. 24, 25. In FIGS. 22 and 23 the elements 41 to 44 are shown in the "straight" or "extended" arrangement of the joint, that is, in a state where the talus implant body 43 and the tibia implant body 44 are at a maximum distance from each other and elements 41 to 44 are centred around the joint axes S—S arranged in line. At its side facing the talus ball element 41 the tibia socket element 42 has the form of a concave part-spherical socket 61, (herein referred to as the tibia socket) comprised within an angle of about 130°. At its side facing the tibia socket element, the talus ball element 41 has the form of part spherical convex body, the so-called talus ball, referenced 51 and which is congruent in form with the socket 61 in the tibia socket element 42. In the mounted state of the artificial ankle joint the talus ball 51 rests in the tibia socket 61 and can freely move in an abutting condition.

Figure 25:
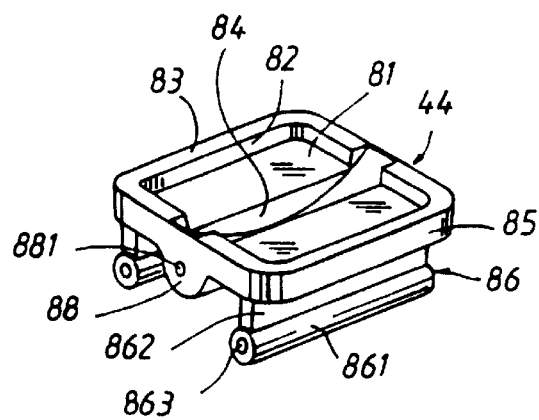
FIG. 25 is a perspective view of a joint holder forming part of the artificial joint of FIG. 22, the joint holder of FIG. 25 being herein referred to as the tibia implant holder.

The tibia socket element 42 has the form, in cross section parallel to the joint axis S—S, of a square with rounded corners. The base of element 42, i.e. the side of the tibia socket element 42 facing away from the tibia socket 61, is best seen in FIG. 26 and is of a form complementary with the side of the tibia implant body 44 facing the joint (FIG. 25).

The portion of the tibia implant body 44 which engages the socket element has the form of a mounting plate with a peripheral shape corresponding to the cross sectional shape of element 42 and thus in the form of a square with rounded off corners. The side of the tibia implant body 44 facing tibia socket element 42 has a recess of similar shape bounded by side walls 82. Reference 83 denotes the top surfaces of walls 82. The tibia implant body 44 has a flat bottom surface 81. The inner surfaces of side walls 82 diverge slightly towards the free edges 83 (uppermost in FIG. 25), i.e. the walls 82 are relieved slightly. The outer surfaces of side walls 82 are referenced 85. The side of the socket element 42 remote from the socket 61 is provided with a rebate 65, 66 (see FIG. 26) around its periphery, to provide a square boss, of a form complementary with the square recess in element 44 and which is received in that recess. This square boss terminates in an end face 67. The rebate around element 42 is also relieved slightly, so said square boss is narrower at end face 67. When the element 42 is fitted to the element 44, the side faces 64 of the tibia socket element 42 are co-planar with the corresponding side faces 85 of element 44 and their contours merge.

A slot 84 extends across the bottom surface 81 across the middle of element 44 from one wall 82 to the opposite wall 82. The slot 84 is of uniform width, is of rectangular cross-section perpendicular to its length and has a concave bottom which has the form of a circular arc as viewed in vertical section along the slot.

FIG. 26 shows in detail the form of the side of element 42 remote from socket 61. With the tibia socket element 42 mounted on the tibia implant body 44 a face 65 of the rebate, lying parallel with end face 67 abuts the top surfaces 83 of walls 82 while the base surface 67 abuts bottom face 81 and the side wall 66 of the rebate 65, 66, and which side wall 66 is inclined slightly inwards tilted in the direction of base surface 67, abuts the similarly inclined inner surfaces of walls 82. A rib 68 of form complementary to slot 84 projects from base surface 67 of element 42 and divides the base surface 67 of element 42 into two similar, substantially rectangular portions. The rib 68 fits into the slot 84 of the tibia implant body 44. The implant body 44 has an integral transverse central ridge 88, of generally semi-cylindrical form, extending across its underside (as viewed in FIGS. 22 to 25) which serves to accommodate the slot 84. The central ridge 88 is parallel with two opposite outer side walls 82 of the tibia implant body 44 and extends between the other opposite outer side walls of the implant body. At both of its ends the central ridge 88 is provided with short, blind bores 881 for application of tools or the like.

The tibia implant body 44 also has, on its underside (as viewed in FIGS. 22 to 25) two integral ribs 86 parallel with ridge 88 and with the side walls 82 adjoining the ribs 86. The ribs 86 have greater height than the central ridge 88 and each has, over its entire length a root portion 861 of circular cross-section and an extension portion or web 862 of reduced thickness relative to the root portion 861 and connecting the root portion 861 with the remainder of the element 44. The curved surface of each root portion 861 may extend through an angle of about 270° about the axis of the root portion. Central axial bores 863 provided with internal threads extend into each root portion 861 from each end thereof. The talus implant body 43 is of low height and is generally circular as viewed along axis S—S in FIG. 23. The body 43 consists of a bottom 71 (see FIG. 28) and a peripheral wall with an outer surface, an inner surface 72 and a flat, annular top surface 73. The inner surface 72 of the peripheral wall is slightly relieved, i.e. is slightly convergent towards the bottom 71 (that is, the surface has the form of a truncated cone), while the outer surface of the peripheral wall has four flattened areas 78 arranged at 90° intervals around the axis S—S of FIG. 23. The bottom 71 is provided with two bores 74, 75 extending into a central ridge 77 formed integrally with the bottom 71, on the underside (as viewed in FIG. 28) of the element 43, said ridge 77 extending between the centres of two mutually opposed flattened areas 78 of the outer surface of said peripheral wall. At both its end the central ridge 77 is provided with short, blind bores 771 which are internally screw threaded.

Parallel with the central ridge 77 of the talus implant body and on either side of this ridge the talus implant body 77 has two integral outer ribs 76 on the underside (as viewed in FIG. 28) of element 43. The outer ribs 76 are of greater depth than the central ridge 77 and each has, over its entire length, a root portion 761 and a web or extension portion 762, the root portion being of greater width than the extension portion and having the cross-sectional form of a segment of a circle comprised within an angle of about 270° about the axis of the root portion. In both ends of each root portion 761 central bores 763 are arranged and provided with inner threads for application of tools or the like. The ribs 76 are thus of a form identical with the ribs 86 of the element 44.

The talus ball element 41 has the form of a unitary body of low height including a cylindrical portion surmounted by the part-spherical portion forming the talus ball 51. The curved peripheral surface 52 of the cylindrical part is interrupted by two flattened areas on opposite sides from each other. At its end remote from the talus ball, the element 41 has a peripheral annular rebate which provides a planar annular face 53 from which a central portion having the form of a frustum of a cone rises. The peripheral, frusto-conical wall 54 or the central portion extending from face 53 is thus slightly inwardly inclined. The central portion has a top surface 55 (as viewed in FIG. 27) which is circular. Two studs 57, 58 of the same size project from the circular end face of said central portion and taper conically towards their free ends. Stud 57 is arranged in the centre of the top surface of the central portion while the stud 58 is offset along a radius of the element 41. The flat areas 59 of the peripheral surface 52 are parallel with the diameter extending through studs 57, 58.

When the talus ball element 41 is mounted on the talus implant body 43, the central portion terminating in surface 55 fits within the recess bounded by the inner surface 72 of the peripheral wall and the annular face 53 abuts the end face 73 of the peripheral wall, the top surface 55 abuts the bottom 71 and the wall 54 engages the complementary inner surface 72 of the peripheral wall. In the bottom 71 of the talus implant body 43 two blind bores 74, 75 are arranged; their location and dimensions correspond to the slightly conical studs 57, 58 of the talus ball element 41 which are received in these bores 74, 75. The bores 74, 75 do not penetrate the bottom 71 because the thickness of the bottom 71 in the area of said bores 74, 75 is increased by the central ridge 77, although elsewhere the bottom 71 is relatively thin.

Preferably the planes of flats 78 are tangential to the part cylindrical surfaces of root portions 761 on the sides of the latter remote from ridge 77.

The shallow recess of the talus implant body 43 which receives the talus ball element 41 and the shallow recess of the tibia implant body 44 which receives the tibia socket element 42, can be covered by respective blanking elements 87 and 79. When applied, the talus blanking element 79 completely covers the front side of the talus implant body 43 intended to receive the talus ball 41, the blanking element having edge-to-edge contact with the top face 73 of the wall 72. The talus blanking element 79 is provided with two blind bores 791 for application of tools for applying or removing the blanking element. In its form the inside (not shown) of talus blanking element 79 is complementary to the "inside" of talus ball element 41 shown in FIG. 27, that is, the portion of the talus ball element 41 which, when the talus implant body 43 is mounted, is in abutment with the latter. The talus blanking element thus comprises elements corresponding to the wall and other elements 53, 54, 55, 57 and 58 of the talus implant body 43.

Figure 30:
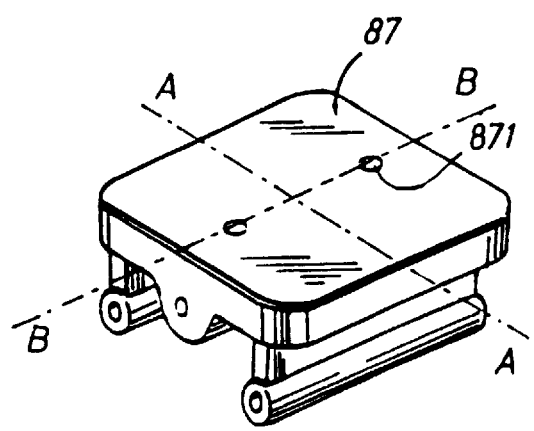
FIG. 30 shows, in perspective, the tibia implant body according to FIG. 25, provided with a detachable cover.
Figure 31:
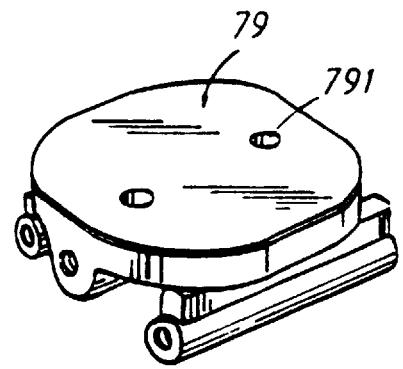
FIG. 31 shows, in perspective, the talus implant body of FIG. 28, provided with a detachable cover.
Figure 32:
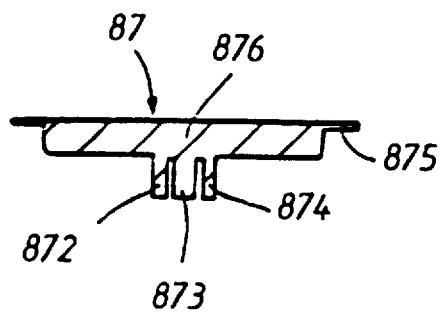
FIG. 32 shows, in perspective, the detachable cover for the tibia implant body according to FIG. 30, in section along the line A—A in FIG. 30, FIGS. 33a to 33f show steps in the replacement of a natural joint by a joint prosthesis in accordance with the present invention.

In the same manner the tibia blanking element 87, when applied, covers the recess of the tibia implant body 44 (FIG. 30). The two blind bores 871 arranged in the outer side are intended for application of tools. In FIG. 32 the tibia blanking element 87 is shown in section. A relatively thin encircling annular rim 875 of the element 87 abuts the end surface 83 of the tibia implant body 44. The thickness of material in a central portion 876 of the blanking element 87 is adapted to the depth of the substantially square shallow recess of the tibia implant body 44. Three parallel ribs 872, 873, 874 having a crescent-like shape in a side view, are arranged on the inner surface of element 87 and are adapted to be received by the slot 84 located in the bottom 81 of the tibia implant body 44. To hold blanking element 87 in place the outer ribs 872, 874 are thinner than the central rib 873 and are slightly resilient.

The root portions 761 and 861 of the talus implant body 43 and the tibia implant body 44, respectively, are insertable in anchoring screws 45 of the general form described above with reference to FIGS. 7 to 10, for example, and thus provided with axial bores and external threads and which have each a longitudinally extending open slot, referenced 91 in FIG. 29, of a width slightly greater than the width of the extension portions 762 and 862, respectively, of implant bodies 43 and 44. In FIG. 22 an anchoring screw 1 is shown in which one of the lateral ribs 76 of the talus implant body 43 has been inserted. The inner bore of the anchoring screw 1 (FIG. 29) is blind. More particularly the screw 1 has axial bores extending from opposite ends and separated by a transverse wall 96 having a thickness of about two external thread turns. In the area of the transverse wall 96 the external thread of anchoring screw 1 is not interrupted. Slot 91 extends over the same length as the longer axial bore while the screw 1 at the insertion end is tapered at 95 and has three symmetrically arranged, longitudinally extending slots 94 opening at the insertion end. The external thread of the anchoring screw 1 is self-tapping. At the application end the anchoring screw 1 is provided with a short internal thread 97.

In the following there is described, with reference to FIGS. 33a to 33f, a procedure for reconstruction of an injured ankle joint using an anchoring assembly as described with reference to FIGS. 22 to 32.

Figure 33A:
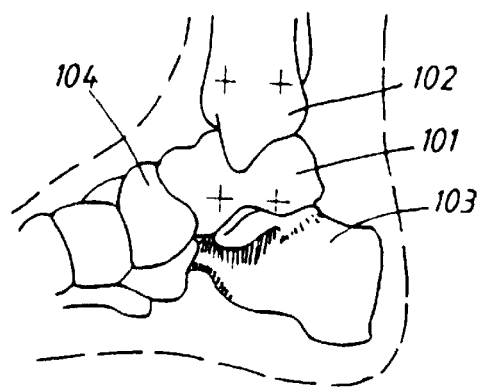
Figure 33B:
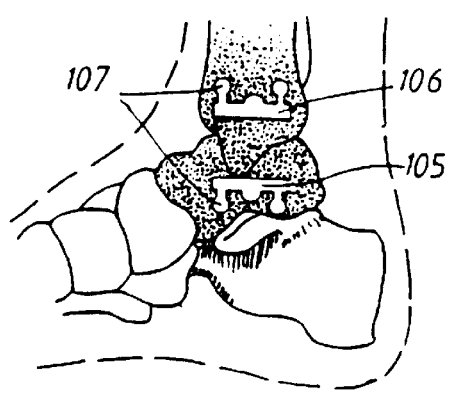
Figure 33C:
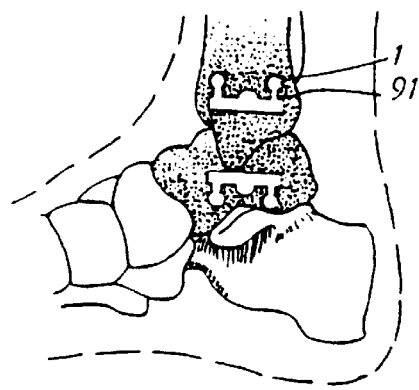
Figure 33D:
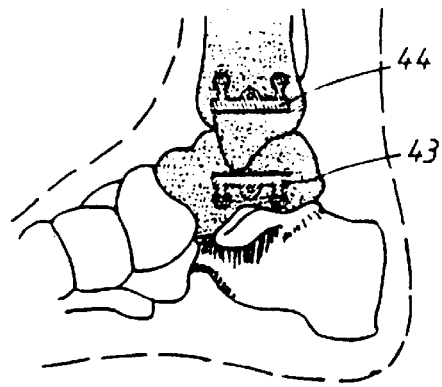

FIG. 33a is a rough representation of the rear part of the skeleton of a human foot in a medial view, wherein the talus is designated by 101, the tibia by 102, the calcaneus by 103, and the navicular bone by 104. In the reconstruction procedure, the talus 101, the distal end of the tibia 102, and the uppermost part of the calcaneus 103 are uncovered medially; by means of a template (not shown) the four points designated by + located at the corners of an imaginary rectangle are marked out (FIG. 33a). At these points four (medially/laterally extending) bores 107 (FIG. 33b) are formed perpendicular to the plane of FIGS. 33a to 33f, each bore having a length corresponding to that of an anchoring screw 1. Thereafter the space designated by 105 is dissected out by starting at the two bores 107 in the talus. A corresponding space designated by 106 is dissected out starting at the two bores 107 in the tibia 102. The contours of spaces 105 and 107 correspond to those of the talus implant element 44, respectively, seen in the direction of longitudinal extension of ribs 76, 77 and 86, 88. The bores 107 are made to a diameter allowing anchoring screws 1 to be screwed into the bores by a self-tapping effect. FIG. 33c shows the position after fitting of the anchoring screws. The screwing process is stopped when the insertion depth of each screw 1 is correct to within one thread pitch. In this process the position of slots 91 is adjusted angularly to make them occupy positions where they are facing each other in pairs (the slots of the talus screws facing the respective tibia screws and the slots of the tibia screws facing the respective talus screws).

In the next step the talus implant body 43 fitted with the blanking element 79 and the tibia implant body 44 fitted with the blanking element 87 are brought in line with the respective pair of anchoring screws and their slots 91, and are inserted into the anchoring screws 1 and the spaces 105, 106 (FIG. 33d) dissected out in the talus 101 and the tibia 102, respectively. The insertion depth can be adjusted by spacer screws (not shown) arranged in the bores 763, 783 at the laterally oriented ends of the lateral ribs 76, 86, and which, in a mounted state, abut the transverse walls 96 of the anchoring screws 1. The talus implant body 43 and the tibia implant body 44 are secured in their inserted position by short stop screws (not shown) which are screwed into the inner threads 97 of the anchoring screws 1 until they abut the medially oriented ends of the lateral ribs 76, 86. It will be understood that any of the other provisions for adjustment and retention of the root portions etc. of prosthesis parts described with reference to FIGS. 7 to 21 may be utilised in this context.

Figure 33E:
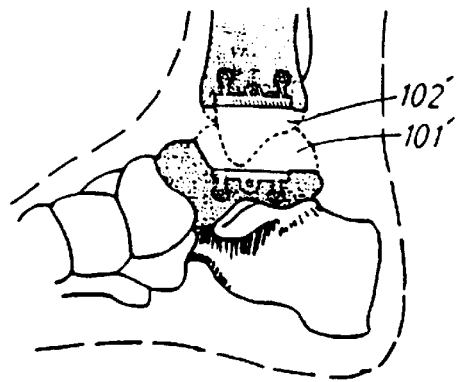
Figure 33F:
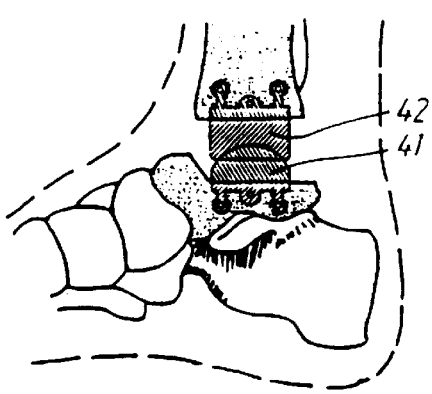

The wound is then closed. After a short healing period, the patient can continue using the injured ankle joint. During a period of several months the anchoring screws 1 with the talus implant body 43 and the tibia implant body 44 progressively become integrated with and anchored in the osseous tissue. When the process of integration is deemed to have progressed far enough the patient is operated on for a second time. On this occasion the portions of the talus and the tibia indicated by dashed lines in FIG. 33e are removed by sections uncovering the talus blanking element 79 and the tibia blanking element 87 which are then removed. This is followed by insertion of the talus ball element 41 and the tibia socket element 42 into the respective recesses in the talus implant body 43 and the tibia implant body 44 and the wound is closed.

The artificial ankle joint can be put under load immediately upon completion of surgery. The patient is thus not required to dispense altogether with an ankle joint retaining at least a fair degree of function for any time. At the same time the integration of the implant in the healing phase and the process of its anchoring in osseous tissue is allowed to proceed undisturbed.

In addition to the disclosed process the artificial ankle joint can also be anchored in a way comprising the arrangement of bores in the talus and/or the tibia in a direction rotated by 90° in respect of the direction disclosed in FIG. 33a, that is, dorsally/anteriorly. In this case it might be necessary to remove a smaller portion of the upper central part of the talus.

In a similar way also other joints can be replaced in part or completely. The anchoring assembly according to the invention is useful, for example for anchoring of knee joint prostheses, hip joint prostheses, axle joint prostheses, elbow joint prostheses and hand joint prostheses.

I claim:

1. A substantially rotationally symmetrical anchoring element intended for implantation in tissue for supporting prostheses or artificial joint components, the anchoring element being comprised of a tissue compatible material, the anchoring element having a peripheral surface which is provided with an external thread, the anchoring element having an insertion end which is the leading end thereof during insertion in tissue, the insertion end being for the attachment of the anchoring element to tissue, the anchoring element having an opposite application end from which prostheses or artificial joint components are attachable to the anchoring element, the anchoring element having a slot defined therein extending radially into the element from one side and only extending partially across the anchoring element and the slot extending substantially axially along a major portion of the axial length of the anchoring element from the application end thereof and ending at a distance from the insertion end, the slot being arranged to receive the prosthesis or artificial joint component.

2. The anchoring element of claim 1, further comprising an emplaceable end releasable blanking element engaged in the slot to shield the slot during the application of the anchoring element into a recess prepared in the tissue and during subsequent healing of the tissue around the anchoring element.

3. The anchoring element of claim 1, in which the slot comprises a track milled in the anchoring element to thereby include lateral edge surfaces of the slot which are adapted for releasable retention of a blanking member.

4. The anchoring element of claim 1 including an inner bore defined in the element for extending from the application end of the anchoring element and communicating with the slot in the radial direction and the slot extending radially from the peripheral surface to the bore.

5. The anchoring element of claim 4 in which the inner bore has a longer axial extension than the slot communicating with the bore.

6. A substantially rotationally symmetrical anchoring element intended for implantation in tissue for supporting prostheses or artificial joint components, the anchoring element being comprised of a tissue compatible material, the anchoring element having a peripheral surface which is provided with an external thread, the anchoring element having an insertion end which is the leading end thereof during insertion in tissue, the insertion end being for the attachment of the anchoring element to tissue, the anchoring element having an opposite application end from which prostheses or artificial joint components are attachable to the anchoring element, the anchoring element having a slot defined therein extending radially into the element and extending substantially axially along a major portion of the axial length along the element from the application end thereof and ending at a distance from the insertion end, the slot being arranged to receive the prosthesis or artificial joint component;

an inner bore defined in the element for extending from the application end of the anchoring element and communicating with the slot in the radial direction and the slot extending radially from the peripheral surface to the bore; and a blanking element which has a root portion shaped and dimensioned to allow it to be inserted in the bore in the element and has an extension portion of reduced thickness substantially the width of the slot extending from the root portion such that the blanking element can be releasably fitted in the anchoring element from the application end with the root portion within the bore and the extension portion of reduced thickness extending through and substantially filling the slot, the blanking element arranged to be temporarily inserted into the anchoring element and removable therefrom for attachment of the prosthesis or artificial joint component.

7. The combination of claim 6 in which the extension portion has coupling means for coupling to prosthesis components or artificial joint components.

8. A substantially rotationally symmetrical anchoring element intended for implantation in tissue for supporting prostheses or artificial joint components, the anchoring element being comprised of a tissue compatible material, the anchoring element having a peripheral surface which is provided with an external thread, the anchoring element having an insertion end which is the leading end thereof during insertion in tissue, the insertion end being the attachment of the anchoring element to tissue, the anchoring element having an opposite application end toward which prostheses or artificial joint components are attachable to the anchoring element, the anchoring element having a slot defined therein extending radially into the element and extending substantially axially along the element from the application end thereof and ending at a distance from the insertion end;

a region of the anchoring element extending to the insertion end being conically tapered and having at least one slit extending along the anchoring element to provide a cutting edge.

\* \* \* \* \*